United States Patent [19]

Kelly

[11] Patent Number: 4,947,862

[45] Date of Patent: Aug. 14, 1990

[54] BODY COMPOSITION ANALYZER

[75] Inventor: Kevin A. Kelly, Columbus, Ohio

[73] Assignee: Danninger Medical Technology, Inc., Columbus, Ohio

[21] Appl. No.: 263,867

[22] Filed: Oct. 28, 1988

[51] Int. Cl.$^5$ .............................................. A61B 5/05
[52] U.S. Cl. .................................................... 128/734
[58] Field of Search ............... 128/723, 734, 795, 796, 128/710; 364/413.02, 413.1; 324/65 R

[56] References Cited

U.S. PATENT DOCUMENTS

| | | | |
|---|---|---|---|
| 2,763,935 | 9/1956 | Whaley et al. | 128/734 |
| 3,347,223 | 1/1964 | Pacela | 128/723 |
| 3,452,743 | 3/1965 | Rieke | 128/734 |
| 3,757,778 | 9/1973 | Graham | 128/696 |
| 3,802,419 | 4/1974 | Yates | 128/723 |
| 3,871,359 | 3/1975 | Pacela | 128/734 |
| 3,882,851 | 5/1975 | Sigworth | 128/723 |
| 4,008,712 | 2/1977 | Nyboer | 128/734 |
| 4,267,576 | 5/1981 | Power et al. | 128/695 |
| 4,557,271 | 12/1985 | Stoller et al. | 128/734 |
| 4,708,146 | 11/1987 | Lane | 128/723 |
| 4,785,812 | 11/1988 | Pihl et al. | 128/419 D |
| 4,793,362 | 12/1988 | Tedner | 128/734 |
| 4,895,163 | 1/1990 | Libke et al. | 128/734 |

OTHER PUBLICATIONS

"Automatic Recording of Biological Impedences", Tedner, Journal of Medical Engineering and Technology, vol. 2, No. 2, Mar. 1978, pp. 70–73.

Millman, *Microelectronics: Digital and Analog Circuits and Systems*, Mc Graw-Hill, Inc., 1979, pp. 406, 593–595, 653–655.

*Primary Examiner*—Max Hindenburg
*Assistant Examiner*—Kennedy J. Schaetzle
*Attorney, Agent, or Firm*—Pearne, Gordon, McCoy & Granger

[57] ABSTRACT

An analyzer determines the amount of body fat on a patient by using a measurement of body impedance is based upon the nature of the conduction of an applied electrical current in the human body. The analyzer has a constant current source circuit for inducing a high frequency low-voltage signal in the body, and magnitude and phase detection circuits for measuring the magnitude and phase shift of the induced signal.

7 Claims, 4 Drawing Sheets

BODY COMPOSITION ANALYZER

BACKGROUND OF THE INVENTION

1. Field of the Invention

This invention relates to electronic devices for the measurement of body fat, and more particularly to those devices which measure body fat by applying a low-level constant RMS value alternating current to the body.

2. Description of the Prior Art

Measurement of body composition is assuming greater importance in assessing nutritional status in both health and disease. Direct measurement of body composition has been limited to research centers using hydrostatic weighing or isotope-dilution techniques. An indirect measurement technique has been developed based upon a determination of body electrical impedance.

The method for determining body impedance is based upon the nature of the conduction of an applied electrical current in the human body. In biological structures, application of a constant, low-level alternating current produces an impedance to the spread of the current that is frequency dependent. The human body contains intra- and extracellular fluids that act as electrical conductors and cell membranes that act as imperfect reactive elements. At low frequencies (around 1 kHz), the current mainly passes through the extracellular fluids, while at higher frequencies (500–800 kHz) it penetrates the intra- and extracellular fluids. Thus, body fluids and electrolytes are responsible for electrical conductance (the inverse of resistance) and cell membranes are involved in capacitance.

The use of bioelectrical impedance measurements to determine fat-free mass is based upon the principle that the impedance of a geometrical system is related to conductor length and configuration, the impedance to the flow of current can be related to the flow of current as $$Z = \frac{pL}{A},$$

where Z is impedance in ohms, p is volume resistivity in ohm-cm, L is conductor length in cm, and A is conductor cross-sectional area in cm². Multiplying both sides of the equation by L/L gives:

$$Z = \frac{pL^2}{AL} = \frac{pL^2}{V},$$

where AL equals the volume V. Rearranging this question yields, $$V = \frac{pL^2}{Z}.$$

In the human body, electrical conduction is related to the water and electrolyte distribution in the biological conductor. Because fat-free mass contains virtually all the water and conducting electrolytes in the body, conductivity is far greater in the fat-free mass that in the fat mass of the body. The electrically determined biological volume V is inversely related to Z, and thus it is also inversely rated to resistance R and reactance Xc, since $$Z = \sqrt{(R^2 + Xc^2)}.$$

Because the magnitude of reactance is small relative to resistance, and resistance is a better predictor of impedance than is reactance, volume can be expressed as $$V = \frac{pL^2}{R},$$

where L is standing height in cm and R is resistance in ohms. Although there are difficulties in applying this general principle in a system with as complex geometry and bioelectrical characteristics as the human body, this relationship has been used to derive models for the prediction of human body composition by assuming that the body is a series of connected cylinders.

Determinations of resistance and reactance have been made using four terminal impedance plethysmographs. Examples of such plethysmographs include the model 101, manufactured by RJL Systems of Detroit, Mich. The four terminal method has been used to minimize contact impedance or skin-electrode interactions. As a general procedure, measurements were made about two hours after eating and within 30 minutes of voiding. The patient, clothed but without shoes or socks, lied supine on a cot. Aluminum foil spot electrodes were positioned in the middle of the dorsal surfaces of the hands and feet proximal to the metacarpal-phalangeal and metatarsal-phalangeal joints, respectively, and also medially between the distal prominences of the radius and the ulna and between the medial and lateral malleoli at the ankle. A thin layer of electrolyte gel was applied to each electrode before application to the skin. An excitation current of 800 µA at 50 kHz was introduced into the patient at the distal electrodes of the hand and foot and the voltage drop was detected by the proximal electrodes.

According to Ohm's Law the electrical impedance Z to alternating current of a circuit was measured in terms of voltage E and current I as $$Z = \frac{E}{I}.$$

Z=E/I.

By using phase sensitive electronics, one could quantify the geometrical components of Z. Resistance R is the sum of in-phase vectors, and reactance Xc is the sum of out-of-phase vectors. A phase discriminator was used to measure the phase angle to produce resistance and reactance measurements.

This technique provided a deep homogenous electrical field in the variable conductor of the body. Determinations of resistance and reactance were made using electrodes placed on the ipsilateral and contralateral sides of the body. The lowest resistance value for an individual was used to calculate conductance (h²/R) and to predict fat-free mass. The accuracy of this method has been found to be within 2%. Statistical models have been developed to estimate total body water and fat-free mass in adults.

To provide an accurate measure of resistance and reactance, it is important to provide a constant current source. Existing plethysmoqraphs have been able to provide a constant current source only by using expensive circuitry. Plethysmographs using less expensive circuitry have been unable to supply a constant current source with the associated accuracy to provide accurate resistance and reactance measurements.

In addition, it is apparent that the measurement device must be properly connected to the body of the patient. If any of the four electrodes is improperly located on the patient's body or is improperly connected to the measurement device, the resulting measurements will be erroneous.

SUMMARY OF THE INVENTION

The present invention provides a body composition analyzer which overcomes the problems of the prior art and provides unique advantages which have not been available before. The body composition analyzer of the present invention includes a constant current source which provides an accurate low-level alternating current signal.

The present invention provides a constant current source circuit comprising a modified Wien bridge oscillator. The signal from the oscillator is fed through an instrumentation amplifier and a full wave rectifier to an error amplifier which provides an error signal to the oscillator to maintain the oscillator in phase at constant current.

In the constant current source circuit of the present invention, the error of the current change is very low, varying by less than 0.5% between 0 K$\Omega$ and 1 K$\Omega$ output resistance. This is four times better than the prior art, which typically had a current source error of 2%.

The present invention also provides a magnitude detection circuit and a phase detection circuit to measure the magnitude and phase lag of the signal induced in the patient by the constant current source. The magnitude detection circuit includes an instrumentation amplifier and a full wave rectifier which are essentially identical to those used in the constant current source network to reduce the effect upon the phase detection circuit.

In the phase detection circuit of the body composition analyzer of the present invention, the circuit compares a sine wave in phase with the constant current signal with a sine wave in phase with the induced voltage. Since both of these signals are offset by the phase lag caused by going through the non-ideal differential amplifiers (which is a function of the operational amplifier processing and the external gain and frequency compensation), the differential amplifiers of both circuits are matched so that the differential phase offset between the two circuits will be at a minimum and so that errors will be minimized.

The body composition analyzer of the present invention is provided with receptacles for the electrodes that are connected to the patient. These receptacles are arranged within the image of a patient's hand and foot, so that the user can quickly and easily determine the proper receptacle for the corresponding electrode. This design reduces the possibility that one of the electrodes will be incorrectly connected to the analyzer, resulting in erroneous readings.

These and other advantages are provided by the body composition analyzer of the present invention. The body composition analyzer comprises four electrodes for connection to a patient. A constant current source circuit is connected to one of the electrodes. The constant current source circuit comprises an oscillator providing an output to the electrode, an instrumentation amplifier connected to the output of the oscillator, and a full wave rectifier connected to the output of the instrumentation amplifier and supplying an error signal to the oscillator. A magnitude detection circuit is connected to two of the electrodes for measuring the current from the electrodes. A phase detection circuit is connected to receive a signal from the constant current source circuit and a signal from the magnitude detection circuit for measuring the phase shift between the two signals. Microcomputer means are connected to the phase detection circuit and the magnitude detection circuit for measuring resistance and reactance of the patient and converting measurements to an indication of the amount of body fat.

The body composition analyzer is contained in a housing which has images of a hand and a foot at the point at which the electrode is connected to the housing in order to assist in properly placing each of the electrodes at the appropriate location on the patient. The housing may also have calibration bars for connection of the ends of the electrodes, and a fixed resistance element connecting the two calibration bars, to permit the analyzer to be calibrated through the electrodes.

DETAILED DESCRIPTION OF THE PREFERRED EMBODIMENT

Figure 1:
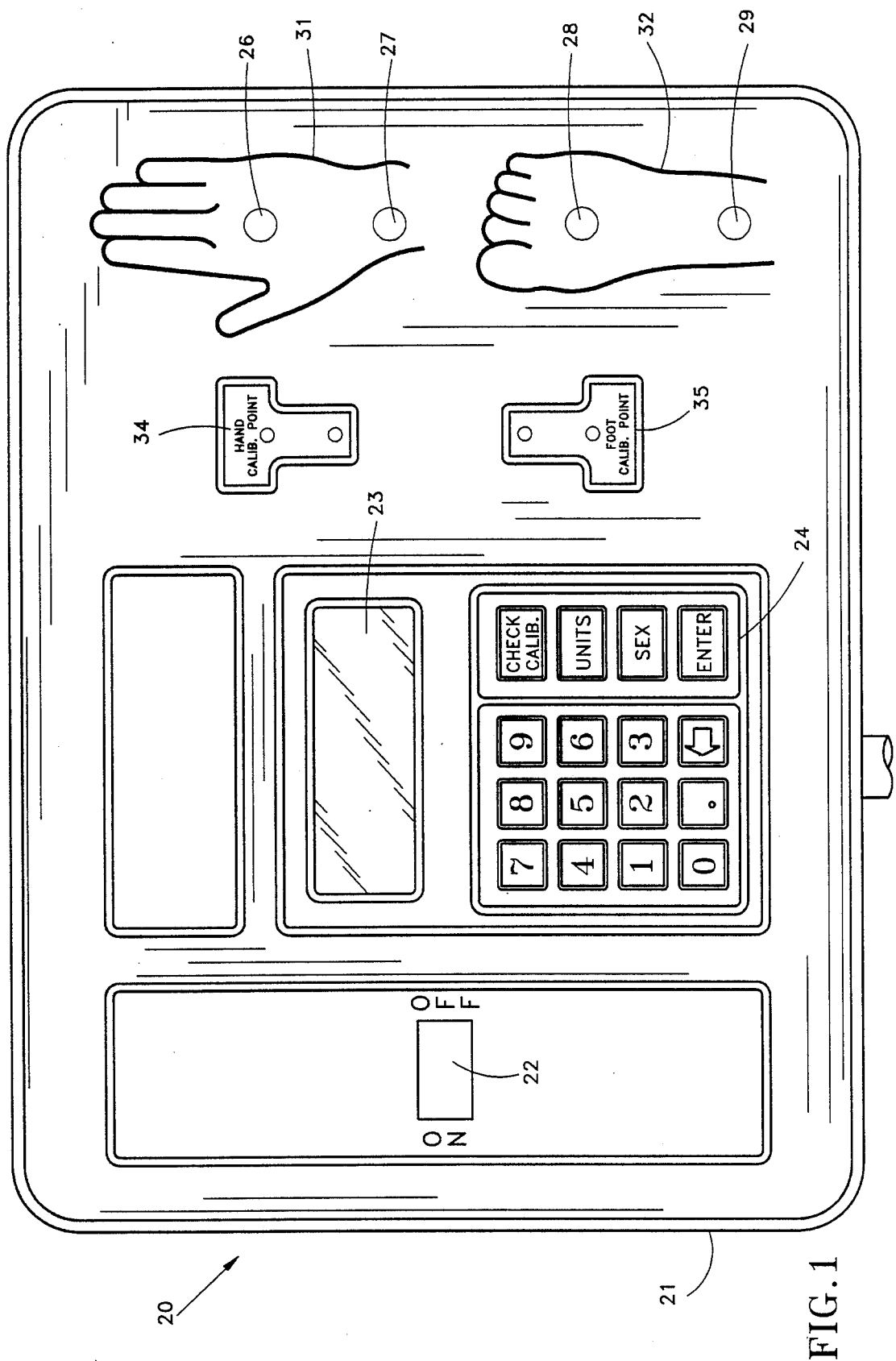
FIG. 1 is a plan view of the housing of the body composition analyzer of the present invention.

Referring more particularly to the drawings, and initially to FIG. 1, there is shown the body composition analyzer 20 of the present invention. The body composition analyzer functions by measuring the resistance and reactance of the human body. Electrodes are placed on the distal and proximal hand and foot. A known constant current, 500 $\mu$A at 50 kHz, is applied by an electrode connected to the distal foot, and goes to ground from an electrode connected to the distal hand. The induced voltage is measured, using high input impedance electrodes connected to the proximal hand and the proximal foot. Height, weight, and age are input, using a keypad, and the body resistance is measured by the circuitry. These variables are used in accordance with known prediction techniques to predict percent body fat.

As shown in FIG. 1, the body composition analyzer 20 of the present invention comprises a housing 21, which includes an on/off power switch 22, a display screen 23, and an input keypad 24. The keypad 24 includes numeric keys for inputting numeric information, such as height, weight and age, and four function keys for designating the type of numeric information input and controlling the operation of the analyzer. The electrodes are connected at four receptacles 26, 27, 28, and 29. The receptacle 26 is for the electrode attached to the distal hand. The receptacle 27 is for the electrode attached to the proximal hand. The receptacle 28 is for the electrode attached to the distal foot. The receptacle 29 is for the electrode attached to the proximal foot.

The receptacles 26–29 are surrounded by graphic indications of the hand and foot of the patient. Specifically, the receptacles 26 and 27 are located on the image 31 of a hand to show the location of connection of the electrodes, and the receptacles 28 and 29 are similarly located on the image 32 of a foot. The hand and foot images 31 and 32 enable the operator to quickly identify the receptacle for each electrode by matching the graphic indication around of the receptacle to the location that the electrode is connected on the patient. This assures that the body composition analyzer will be properly connected to the patient and that the measurements will be accurately received.

The analyzer is also provided with two calibration bars 34 and 35 which are used to verify that the unit is in proper calibration. One calibration bar 34 is provided for the hand electrodes, and the other calibration bar 35 is provided for the foot electrodes. An appropriate resistance element, e.g., 511 ohms, is provided between the calibration bar 34 and the calibration bar 35. By connecting the electrodes to the calibration bars 34 and 35, and setting the analyzer in its calibration mode, the analyzer provides the user with an accuracy indication.

Figure 2:
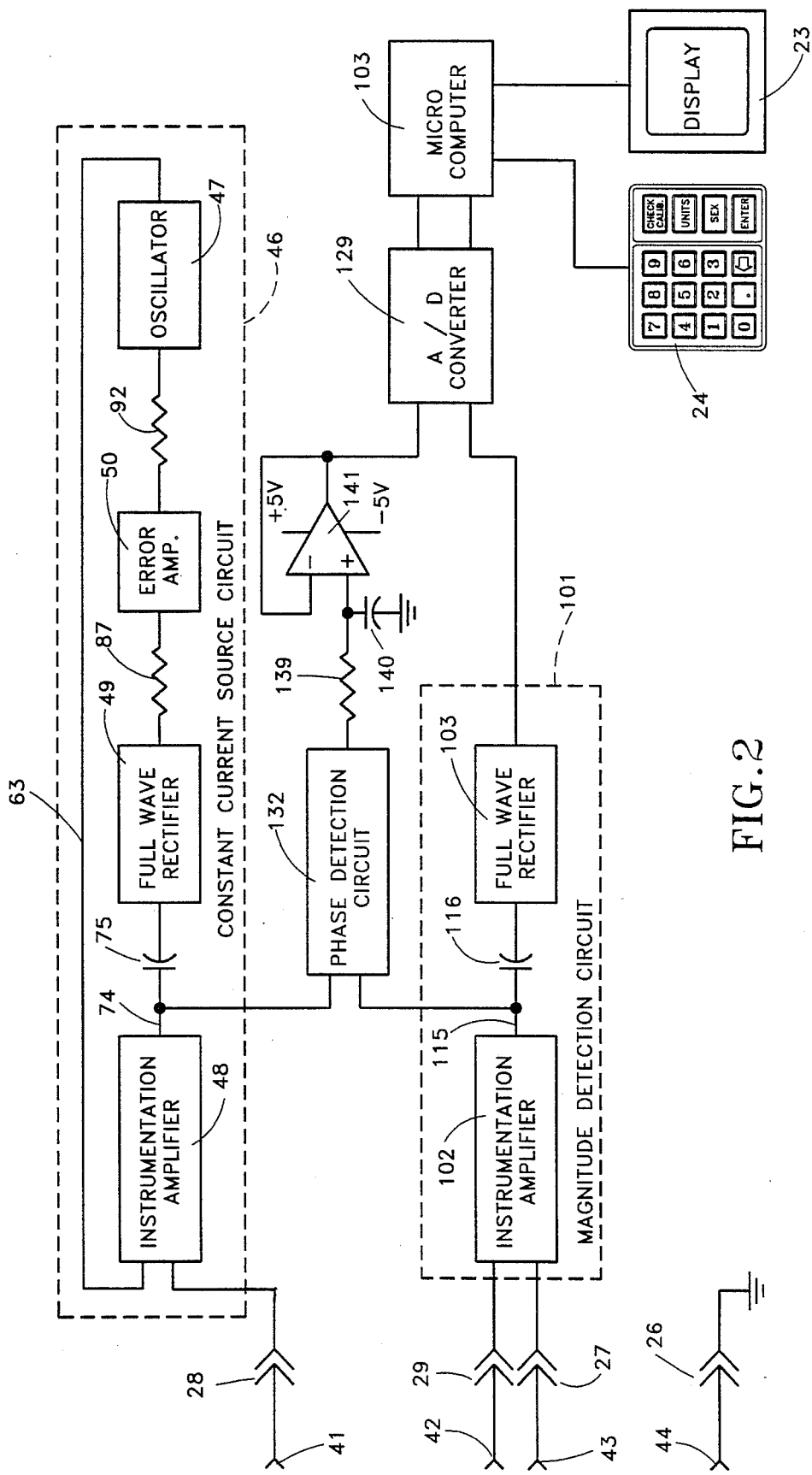
FIG. 2 is a block diagram showing the electronic components of the body composition analyzer of the present invention.

The internal circuitry of the body composition analyzer 20 of the present invention is shown in schematic form in FIG. 2. The analyzer 20 includes four electrodes 41, 42, 43, and 44 for connection to the body of the patient. The electrode 41 is used for attachment to the distal foot, and provides a constant current input to the patient's body. The electrode 44 is attached to the distal hand, and is connected by means of the receptacle 26 to ground. The electrodes 42 and 43 are connected to the proximal foot and hand, respectively, and provide the inputs to the body composition analyzer for the measurement of resistance and reactance of the body.

As shown in FIG. 2, the distal foot electrode 41 is connected by means of the receptacle 28 to a constant current source circuit 46. The constant current source circuit 46 comprises an oscillator 47 providing output to a differential amplifier or instrumentation amplifier 48. The output of the instrumentation amplifier 48 is fed back to the oscillator 47 through a full wave rectifier 49 and an error amplifier 50.

Figure 3:
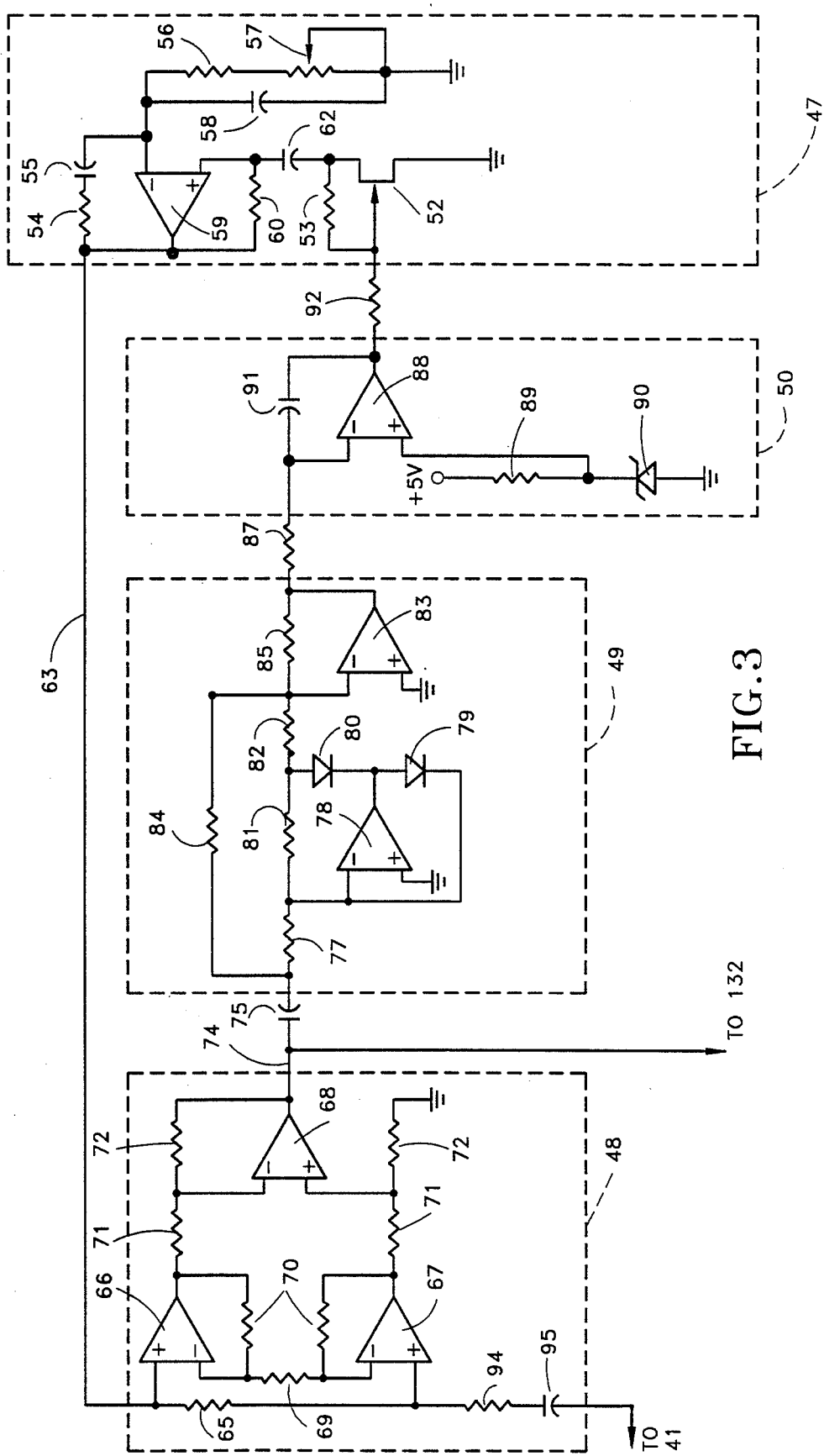
FIG. 3 is a detailed electrical schematic diagram showing a portion of the components of FIG. 2.

The details of the constant current source circuit 46 can be seen in FIG. 3. The oscillator 47 is a modified Wien bridge oscillator comprising an N-channel JFET 52 used as a voltage-controlled resistor. A 20 KΩ resistor 53 is connected around the JFET 52. Wien bridge oscillators are well known and widely used and take advantage of the fact that the phase of the voltage across the parallel branch of a series and a parallel RC network connected in series is the same as the phase of the applied voltage across the two networks at one particular frequency and that the phase lags with increasing frequency and leads with decreasing frequency. A 3.16 KΩ resistor 54 and a 1000 pF capacitor 55 provide the series RC network, and a 2.74 KΩ fixed resistor 56 and 1 KΩ calibration resistor 57 and a 1000 pF capacitor 58 provide the parallel RC network. An operational amplifier 59 is connected in parallel with the resistor 54 and the capacitor 55. A 15 KΩ gain resistor 60 is provided between the output and the inverting input of the operational amplifier 59.

The JFET 52 provides the inverting input to the operational amplifier 59. Between the JFET 52 and the operational amplifier 59 is a 1 µF capacitor 62 which is a low frequency roll-off capacitor preventing offset voltage and offset current errors from being multiplied by the amplifier gain. The output of the operational amplifier 59 is fed on a line 63 to the instrumentation amplifier 48.

As shown in FIG. 3, the oscillating output on the line 63 causes a current flow across a 412 Ω resistor 65. The differential amplifier or instrumentation amplifier 48 actually comprises three operational amplifiers 66, 67, and 68. A 1.65 KΩ gain resistor 69 connects the inverting inputs of the amplifiers 66 and 67 while the outputs of the amplifiers 66 and 67 are each connected to the inverting input through matched resistors 70. The outputs of the amplifiers 66 and 67 are connected to the inputs of the amplifier 68 through matched resistors 71, and the inputs of the amplifier 68 are connected to the amplifier output (for the inverting input) or to ground (for the noninverting input) through matched resistors 72. The output of the operational amplifier 68 provides the output of the instrumentation amplifier 48 and can be described by the relationship:

$$E_{OUT} = [E_{IN}^+ - E_{IN}^-]\left[\frac{2R_1}{R_G} + 1\right]\left[\frac{R_3}{R_2}\right],$$

where $E_{OUT}$ is the output of the amplifier 68, $E_{IN}^-$ is the input to the amplifier 66, $E_{IN}^+$ is the input to the amplifier 67, $R_G$ is the value of the gain resistor 69, $R_1$ is the value of the resistor 70, $R_2$ is the value of the resistor 71, and $R_3$ is the value of the resistor 72.

The gain of the instrumentation amplifier 48 is determined by the value of the resistor 69, and the value of the resistor 69 does not affect the common mode error signal. Thus, common mode rejection theoretically increases in direct proportion to gain. Furthermore, common-mode signals are only amplified by a factor of one regardless of gain because no common-mode voltage will appear across the resistor 69, hence no common-mode current will flow in it. This means that large common-mode signals can be handled independent of gain. Because of the symmetry of the instrumentation amplifier 48, first order common-mode error sources in the operational amplifiers 66 and 67 tend to be cancelled out by the operational amplifier 68.

The output of the instrumentation amplifier 48 is provided on a line 74 which is connected to a 0.1 µF capacitor 75. The capacitor 75 eliminates direct-current offsets. This output is then provided to the full wave rectifier 49.

As shown in FIG. 3, the full wave rectifier 49 comprises the input signal applied through an input resistor 77 to the summing node of an inverting operational amplifier 78. The output of the operational amplifier 78 is connected back to the same input through a diode 79. The output is also provided through another diode 80. When the input signal is positive, the diode 80 is forward-biased and develops an output signal across a resistor 81. As with any inverting amplifier, the gain is equal to the ratio of resistances of the resistor 81 divided by the input resistor 77. When the signal goes negative, the diode 80 is nonconducting and there is no output. However, a negative feedback path is provided by the diode 79. The path through the diode 79 reduces the positive output swing and prevents the amplifier 78 from saturating. The operational amplifier 78 and the diodes 79 and 80 together provide a half-wave rectifier, the output of which is then provided through a resistor 82 to an inverting amplifier 83. The amplifier 83 sums the half-wave rectified signal from the resistor 82 and the input signal provided through a resistor 84 to provide a full wave output. A gain resistor 85 connects the output of the amplifier 83 to the inverting input.

For negative input signals, the output of the amplifier 78 is zero, no current flows through the resistor 82, and the output of the amplifier 83 is $$E_{OUT} = -\frac{R_4}{R_5} E_{IN},$$

where $E_{OUT}$ is the output of the amplifier 83, $E_{IN}$ is the input to the resistor 77, $R_4$ is the value of the resistor 85, and $R_5$ is the value of the resistor 84. For positive input signals, the amplifier 83 sums the current through the resistors 82 and 84 and $$E_{out} = R_4 \left[ \frac{E_{IN}}{R_6} - \frac{E_{IN}}{R_5} \right],$$

where $E_{OUT}$ is the output of the amplifier 83, $E_{IN}$ is the input to the resistor 77, $R_4$ is the value of the resistor 85, $R_5$ is the value of the resistor 84, and $R_6$ is the value of the resistor 82.

The output of the full wave rectifier 49 feeds the error amplifier 50 through a 10 KΩ resistor 87. The error amplifier 50 comprises an operational amplifier 88 receiving an inverting input from the full wave rectifier 49 and receiving a noninverting input from a band gap reference voltage source extracted between a 100 KΩ resistor 89 and a Zener diode 90, providing a 1.235 volt band gap reference voltage. A 0.1 μF capacitor 91 in parallel with the amplifier 88 provides filtering. The operational amplifier 88 compares the band gap reference voltage to that provided from the full wave rectifier 49. The output of the amplifier 88 is provided through a 20 KΩ resistor 92 to the JFET 52 and is used to adjust the channel voltage of the JFET 52 and adjust the oscillator 47 to eliminate the error.

The operational amplifiers 59, 66, 67, 68, 78, 83 and 88 are preferably formed of OP-471 low-noise operational amplifiers manufactured by Precision Monolithics Inc. of Santa Clara, Calif.

To explain the operation of the constant current source circuit 46, at power up, the noninverting input of the amplifier 88 quickly goes to 1.235 volts because the diode 90 provides a 1.235 volt band gap reference. Meanwhile, the inverting input stays near ground. This causes the output of the amplifier 88 of the error amplifier 50 to go to the positive rail. A positive signal on the gate of the JFET 52 causes the channel resistance to lower, thus lowering the voltage at the inverting input of the operational amplifier 59. This lowering of the negative feedback causes the oscillator 47 to output a rail-to-rail square wave on the line 63. The square wave results in a current flow across the resistor 65. The voltage across this resistor 65 is amplified by the instrumentation amplifier 48, rectified by the full wave rectifier 49, and provides an input to the error amplifier 50. The error amplifier 50 compares the band gap reference voltage to that received from the full wave rectifier 49 and adjusts the channel voltage of the JFET 52 to eliminate the error. As the error decreases, the output of the oscillator 47 becomes a sine wave. To maintain control in all situations, the JFET 52 operates at a negative gate voltage of −1 volts, thus allowing swings in either direction.

The constant current source circuit 46 provides a constant current output through a 3.16 KΩ resistor 94 and a 0.1 μF capacitor 95 to the distal foot electrode 41.

An advantage of the circuit is that it is immune to the 60 Hz pick-up. In some prior art circuits, where the patient is in the feedback loop of an operational amplifier, the patient lead would feed directly into the input of the operational amplifier, and this would cause the pick-up of the 60 Hz signal. In the present invention, the patient is not in the feedback loop, so that a constant current source is maintained without the 60 Hz signal being picked up.

Among the other advantages of the constant current source circuit of the present invention is that the error of the current change is very low, varying by less than 0.5% between 0 KΩ and 1 KΩ output resistance. This is four times better than the prior art, which typically had a current source error of 2%. The error of the constant current source is very low because of the high differential gain of the amplifier 88 of the error amplifier 50. The OP-471 component used as the amplifier 88 has a typical DC gain of 500,000 V/V.

Referring again to FIG. 2, the electrodes 42 and 43 which receive input from the proximal foot and proximal hand, respectively, are connected to a magnitude detection circuit 101 by means of the receptacles 27 and 28. The magnitude detection circuit 101 comprises a differential amplifier or instrumentation amplifier 102 and a full wave rectifier 103.

Figure 4:
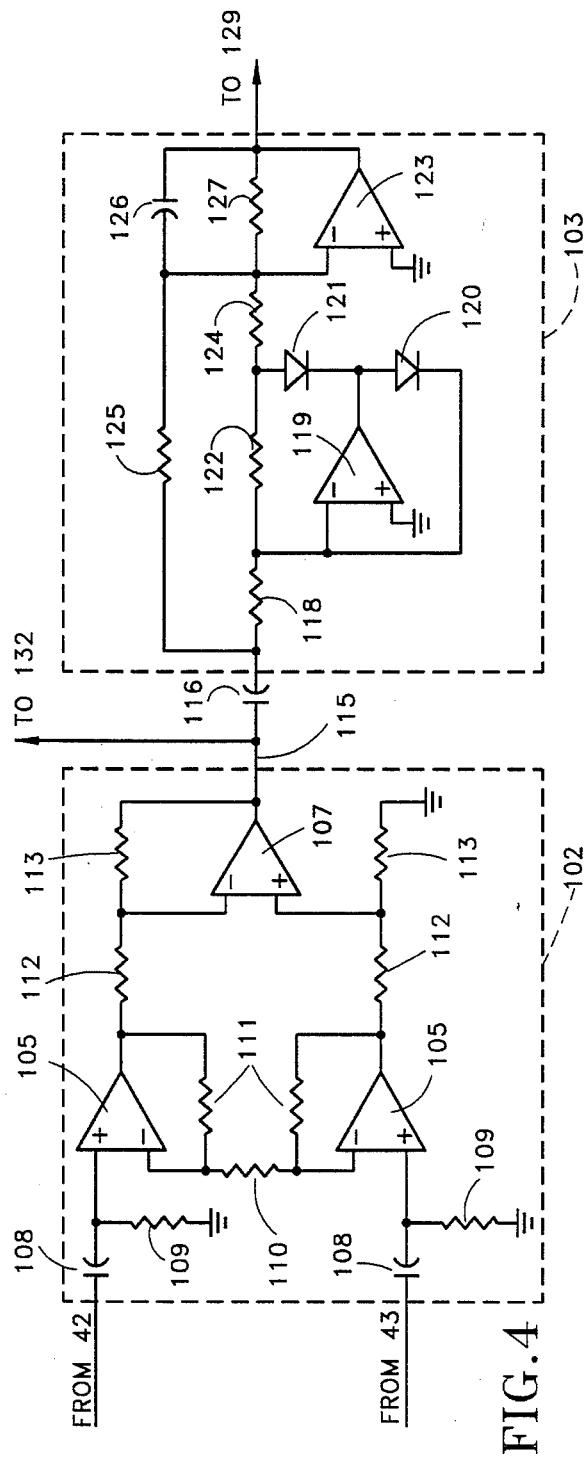
FIG. 4 is another detailed electrical schematic diagram showing another portion of the components of FIG. 2.

As shown in more detail in FIG. 4, the instrumentation amplifier 102 is essentially the same as the instrumentation amplifier 48, comprising three operational amplifiers 105, 106, and 107. The pickup from the electrodes 42 and 43 is fed to the noninverting inputs of the amplifiers 105 and 106, respectively, after passing through 0.1 μF capacitors 108 which are provided to filter direct current signals. A pair of 1 MΩ resistors 109 are provided to keep the noninverting input to the amplifiers 105 and 106 from floating due to input bias current. A 1.65 KO gain resistor 110 connects the noninverting inputs of the amplifiers 105 and 106 and is essentially the same as the gain resistor 69 of the instrumentation amplifier 48. Similarly, matched resistors 111, 112 and 113 perform the same function as the matched resistors 70, 71 and 72 of the instrumentation amplifier 48.

The instrumentation amplifier 102 takes the voltage induced in the patient by the electrode 41 from the constant current source circuit 46 and picked up by the electrodes 42 and 43 and amplifies it. This amplified voltage is fed on line 115 through a 0.1 μF capacitor 116 to the full wave rectifier 103.

The full wave rectifier 103 is essentially the same as the full wave rectifier 49 and comprises an input resistor 118, an operational amplifier 119, diodes 120 and 121, and a resistor 122. Together, these elements form the half-wave rectifier which feeds an amplifier 123. The amplifier 123 receives the half wave signal through from the amplifier 119 through a resistor 124 and receives the input signal through a resistor 125. A 0.1 μF capacitor 126 is placed across the resistor 127 and rolls off the frequency response of the amplifier 123 to give an output equal to the average value of the input. This provides filtering or averaging to obtain a pure DC output. The filter time constant is RC, using the resistor 127 and the capacitor 126, and must be much greater than the maximum period of the input signal.

The filtered output of the full wave rectifier 103 of the magnitude detection circuit 101 is provided to an analog-to-digital (A/D) converter 129, which then provides a digital indication of the measured voltage to a microcomputer 130. The microcomputer 130 also receives input from the keypad and provides output through the display 23.

Figure 5:
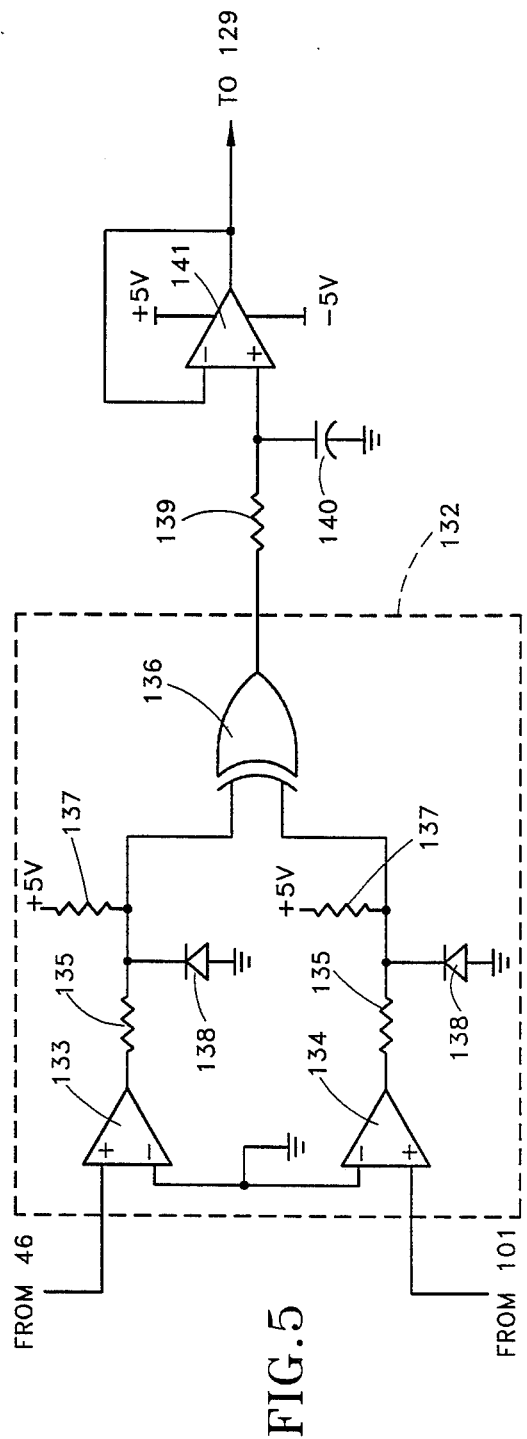
FIG. 5 is another detailed electrical schematic diagram showing another portion of the components of FIG. 2.

As shown in FIG. 2, the output of the instrumentation amplifier 48 of the constant current source circuit 46 and the output of the instrumentation amplifier 102 of the magnitude detection circuit 101 both feed a phase detection circuit 132 which measures the phase angle between the input constant current signal and the induced signal to produce resistance and reactance measurements. As shown in more detail in FIG. 5, the phase detection circuit 132 comprises a pair of comparators 133 and 134 which square up the sine waves received from the instrumentation amplifiers 48 and 102. The instrumentation amplifier 48 outputs a sine wave in phase with the constant current signal, while the instrumentation amplifier 102 outputs a sine wave in phase with the induced voltage. However, both are offset by the phase lag caused by going through the non-ideal differential amplifiers (which is a function of the operational amplifier processing and the external gain and frequency compensation). To minimize these errors, the differential amplifiers of both sections are matched so that the differential phase offset between the two sections will be at a minimum. As with the operational amplifiers 59, 66, 67, 68, 78, 83 and 88 of the constant current source circuit 46, the operational amplifiers 105, 106, 107, 119 and 123 of the magnitude detection circuit 101 are also preferably formed of OP-471 low-noise operational amplifiers manufactured by Precision Monolithics Inc. of Santa Clara, Calif.

The comparators 133 and 134 feed an exclusive-OR gate 136 through 10 KΩ resistors 135. The 10 KΩ resistors 137 and diodes 138 are provided for filtering. The output of the exclusive-OR gate is RC-filtered (by means of a 100 KΩ resistor 139 and a 0.1 μF capacitor 140) and buffered by an operational amplifier 141. The exclusive-OR gate 136 operates on a five-volt power supply, so that a 90-degree phase shift causes a 2.5 volts output to the A/D converter 129.

The microcomputer 130 receives a measurement of the induced voltage through the magnitude detection circuit 101 as converted by the A/D converter 129 and receives a measurement of the phase shift from the phase detection circuit 132 as converted by the A/D converter 129. Height, weight, and age are input, using the external keypad 24. The microcomputer 130 then calculates the percent of body fat, using the resistance and phase shift information and the input data in accordance with known calculations. The results are displayed through the output display device 23.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way this is inconsistent with the extent to which the progress in the art has been advance by the invention.

What is claimed is:

1. A body composition analyzer comprising: four electrodes for connection to a patient; a constant current source circuit connected to one of the electrodes, the constant current source circuit comprising:
an oscillator providing an output to the one of the electrodes;
an instrumentation amplifier connected to the object of the oscillator; and
a full wave rectifier connected to the output of the instrumentation amplifier and supplying an error signal to the oscillator;
a magnitude detection circuit connected to two of the electrodes for measuring the current from the electrodes;
a phase detection circuit connected to receive two signals, one signal from the constant current source circuit and the other signal from the magnitude detection circuit, the phase detection circuit measuring the phase shift between the two signals; and
microcomputer means connected to the phase detection circuit and the magnitude detection circuit for measuring resistance and reactance of the patient and converting measurements to an indication of the amount of body fat.

2. A body composition analyzer as defined in claim 1, wherein the constant current source circuit comprises in addition an error amplifier connected to the output of the full wave rectifier for amplifying the signal from the full wave rectifier and supplying the error signal to the oscillator.

3. A body composition analyzer as defined in claim 1, wherein the magnitude detection circuit contains a second instrumentation amplifier which has components matched exactly to those in the instrumentation amplifier of the constant current source circuit, and wherein the instrumentation amplifier of the magnitude detection circuit and the instrumentation amplifier of the constant current source circuit provide the signals to the phase detection circuit.

4. A body composition analyzer as defined in claim 1, wherein the oscillator of the constant current source is a Wien bridge oscillator.

5. A body composition analyzer as defined in claim 1, comprising in addition a housing containing the constant current source circuit, the magnitude detection circuit, the phase detection circuit and the microcomputer means, the electrodes being connected to the housing through connections, the housing having means for assisting in properly placing each of the electrodes at the appropriate location on the patient, the assisting means including images of a hand and a foot at the connections.

6. A body composition analyzer as defined in claim 5, comprising in addition means for calibrating the analyzer through the electrodes, the calibrating means including calibration bars on the housing for connection of the ends of the electrodes, and a fixed resistance element connecting the calibration bars.

7. A body composition analyzer as defined in claim 1, comprising in addition means for connecting the electrodes to the constant current source circuit and to the magnitude detection circuit and for assisting in properly placing each of the electrodes at the appropriate location on the patient, the connecting and assisting means including an image of a hand and a foot where the electrodes are connected to the circuits.

* * * * *

UNITED STATES PATENT AND TRADEMARK OFFICE
CERTIFICATE OF CORRECTION

PATENT NO. : 4,947,862

DATED : August 14, 1990

INVENTOR(S) : Kevin A. Kelly

It is certified that error appears in the above-identified patent and that said Letters Patent is hereby corrected as shown below:

Column 2, line 48, delete "Z = E/I" (lower).

Column 8, line 44, "KO" should be --K$\Omega$--.

Signed and Sealed this

Seventh Day of January, 1992

Attest:

HARRY F. MANBECK, JR.

*Attesting Officer*      *Commissioner of Patents and Trademarks*